(12) United States Patent
Gibby et al.

(10) Patent No.: US 9,978,027 B2
(45) Date of Patent: May 22, 2018

(54) PRODUCTIVITY MONITORING

(71) Applicant: Novarad Corporation, American Fork, UT (US)

(72) Inventors: Wendell Arlen Gibby, Mapleton, UT (US); Brent Matthew Glover, Saratoga Springs, UT (US)

(73) Assignee: Novarad Corporation, American Fork, UT (US)

( * ) Notice: Subject to any disclaimer, the term of this patent is extended or adjusted under 35 U.S.C. 154(b) by 908 days.

(21) Appl. No.: 14/088,302

(22) Filed: Nov. 22, 2013

(65) Prior Publication Data

US 2014/0149133 A1    May 29, 2014

Related U.S. Application Data

(60) Provisional application No. 61/729,583, filed on Nov. 24, 2012.

(51) Int. Cl.
| | |
|---|---|
| *G06F 15/02* | (2006.01) |
| *G06Q 10/00* | (2012.01) |
| *G06Q 50/22* | (2018.01) |
| *G06Q 30/00* | (2012.01) |
| *G06Q 50/00* | (2012.01) |
| *G06Q 10/06* | (2012.01) |

(52) U.S. Cl.
CPC .  *G06Q 10/063114* (2013.01); *G06Q 10/0639* (2013.01); *G06Q 50/22* (2013.01); *G16H 40/20* (2018.01)

(58) Field of Classification Search
CPC .. G06Q 10/06; G06Q 10/06398; G06Q 50/22; G06F 19/327; G06F 50/22
USPC .......................................................... 705/2–3
See application file for complete search history.

(56) References Cited

U.S. PATENT DOCUMENTS

| | | | |
|---|---|---|---|
| 2006/0282302 A1* | 12/2006 | Hussain ................. | G06Q 10/06 705/2 |
| 2008/0262882 A1* | 10/2008 | Farrell ................... | G06F 19/322 705/7.32 |
| 2009/0204434 A1* | 8/2009 | Breazeale, Jr. ........ | G06F 19/328 705/3 |
| 2011/0218815 A1* | 9/2011 | Reiner ................... | G06Q 50/22 705/2 |

(Continued)

OTHER PUBLICATIONS

Malik, Are You Experiencing Data Overload?, Jul. 2007, Health Purchasing News, pp. 1-4.*

(Continued)

*Primary Examiner* — Joy Chng
(74) *Attorney, Agent, or Firm* — Thorpe North & Western, LLP.

(57) ABSTRACT

A method for monitoring productivity may include monitoring performance of a medical procedure at a local device. Medical procedure data may be received at the local device from a management device. The medical procedure data may include relative value units (RVUs) associated with the medical procedure. Medical professional productivity data related to the medical procedure may be provided for display at the local device based on the monitoring of the performance of the medical procedure and the medical procedure data. A procedure completion notification may be transmitted from the local device to the management device when the medical procedure is completed.

20 Claims, 5 Drawing Sheets

(56) References Cited

U.S. PATENT DOCUMENTS

2013/0262132 A1* 10/2013 Sant ................ G06Q 10/06398
705/2

OTHER PUBLICATIONS

Kaplan et al., The Big Idea: How to Solve the Cost Crisis in Health Care, Sep. 2011, Harvard Business Review, pp. 1-31.*
Silverman, Understanding Productivity-Based Incentives, Feb. 15, 2011, Emergency Physicians Monthly, pp. 1-5.*
MedFocus, Compliance and Production, Sep. 10, 2010, pp. 1-2.*
Google search results: running daily total RVUs, pp. 1-2.*
Malik, Are You Experiencing Data Overload?, Jul. 2007, Health Purchasing News, pp. 1-4 (Year: 2007).*
Kaplan et al., The Big Idea: How to Solve the Cost Crisis in Health Care, Sep. 2011, Harvard Business Review, pp. 1-31 (Year: 2011).*
Silverman, Understanding Productivity-Based Incentives, Feb. 15, 2011, Emergency Physicians Monthly, pp. 1-5 (Year: 2011).*
MedFocus, Compliance and Production, Sep. 10, 2010, pp. 1-2 (Year: 2010).*
Google search results: running daily total RVUs, pp. 1-2 (Year: 2016).*

* cited by examiner

PRODUCTIVITY MONITORING

PRIORITY CLAIM

Priority is claimed to U.S. Provisional Patent Application Ser. No. 61/729,583, filed Nov. 24, 2012, which is hereby incorporated herein by reference in its entirety.

BACKGROUND

Improvement in worker productivity has been a goal of many enterprises. The field of medicine is an example field where productivity of medical professionals is tracked both for determining how much a medical professional is to be paid based on productivity and for determining how much money to charge to a health management organization (HMO), the government or patients for a medical procedure. A variety of ways of calculating medical professional productivity and compensation have been proposed, some of which have been implemented to greater or lesser extents and with differing results. One way of calculating medical professional productivity may include volume-based metrics attached to the number of patients a medical professional treats or the amount of revenue the medical professional bills or collects.

Recently, medical professional productivity and compensation has trended toward models based on Relative Value Units (RVUs). RVUs may reflect a relative level of time, skill, training and/or intensity of a medical professional to provide a given service. RVUs may be used to calculate the volume of work or effort expended by a medical professional in treating patients, evaluating reports and so forth. Different medical procedures may be assigned different RVUs, based on time, skill needed, procedure complexity, and so forth. For example, surgical procedures may have a higher RVU than well child visits. As a result, medical professionals may receive compensation based on a number of procedures performed and a complexity of the procedures, rather than a number of patients seen or billings collected.

There are a variety of RVU formulas being used for determining medical professional compensation. Formulas used in calculating compensation or bonuses of medical professionals may be complicated or confusing and medical professionals may find calculating productivity, efficiency, compensation and so forth to be difficult, as well as determining how to focus efforts to maximize compensation.

DETAILED DESCRIPTION

Figure 1:
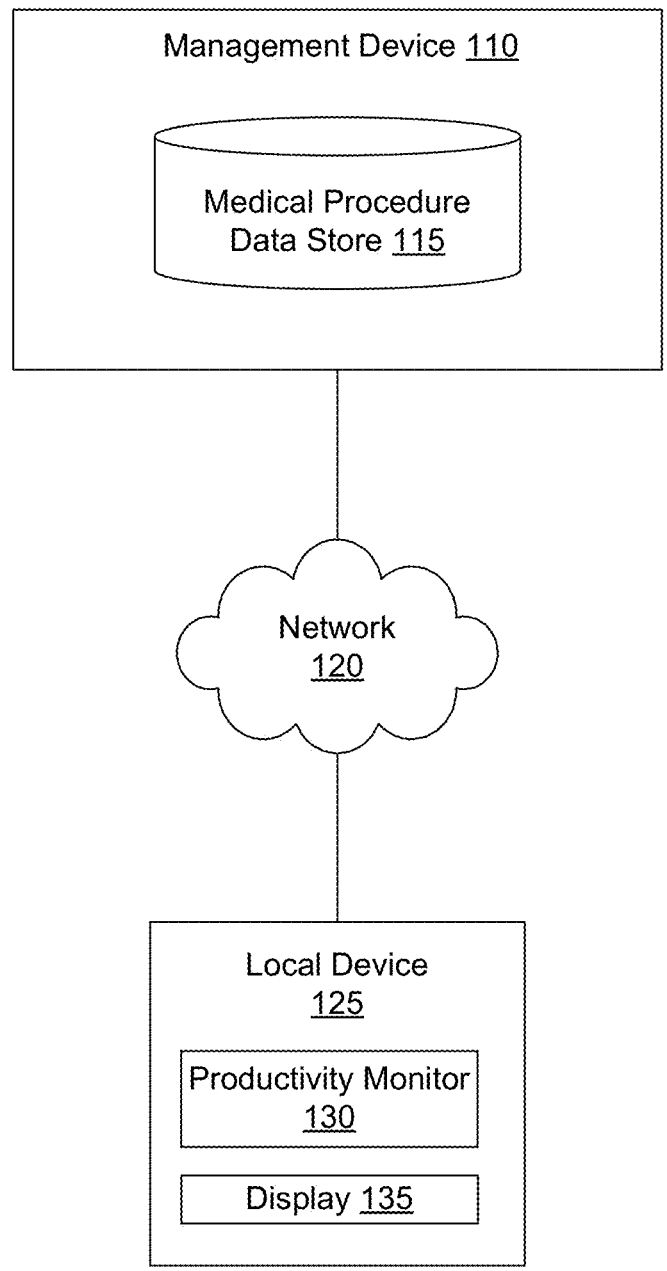
FIG. 1 is a block diagram of a productivity monitoring system in accordance with an example of the present technology.

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

Definitions

As referred to herein, a "medical professional" may include physicians, physician assistants, nurse medical professionals, medical specialists, and any of a variety of other types of health care professionals.

As referred to herein, a "medical procedure" may include the science or practice of the diagnosis, treatment, and prevention of disease. A medical procedure may encompass a variety of health care practices intended to maintain and/or restore health by the prevention and treatment of illness in human beings. A medical procedure may also apply to tasks relating to health science, biomedical research, and medical technology to diagnose and treat injury and disease, such as through medication or surgery, as well as through therapies such as psychotherapy, traction, prostheses, biologics, ionizing radiation and so forth.

While the present technology is described in terms of medicine, the technology may alternately be applied in other areas of technology, science, etc. in which productivity is measured, such as according to a type of unit indicative of time, effort, skill, and so forth involved in completing a task.

It is noted that, as used in this specification and the appended claims, the singular forms "a," "an," and "the" include plural referents unless the context clearly dictates otherwise.

As used herein, a plurality of components may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Examples of the Technology

It is noted in the present disclosure that when describing the system, or the related devices or methods, individual or separate descriptions are considered applicable to one other, whether or not explicitly discussed in the context of a particular example or embodiment. For example, in discussing a device per se, other device, system, and/or method embodiments are also included in such discussions, and vice versa.

Furthermore, various modifications and combinations can be derived from the present disclosure and illustrations, and as such, the following figures should not be considered limiting.

The present technology may provide productivity monitoring. Productivity monitoring may include monitoring the performance of a medical procedure. In accordance with one example, a relative value unit (RVU) associated with the medical procedure may be identified. Medical professional productivity data related to the medical procedure may be provided for immediate or instantaneous display in order to provide feedback to a medical professional. A procedure completion notification may also be transmitted from a local device to a management device when the medical procedure is completed.

Productivity data may be provided and updated in real time, and the productivity data may enable the medical professional to gauge performance for a specific time period (e.g. day, week, month, etc.). Performance may be monitored in real-time for a day at any given time during the day to determine, for example, to allow a medical professional to decide whether to try to work harder to meet a minimum daily goal or threshold number of RVUs (which goal/threshold may also be displayed with the productivity data). The provision of up-to-date productivity data on demand may further assist the medical professional in allocation of resources, focusing on an area of practice and so forth. The up-to-date productivity data may further affect a motivation, productivity, or behavior of the medical professional because productivity, money earned and similar measures may be made available and visible to the medical professional in an accessible and readily understandable format.

In one example, referring to FIG. 1, the present technology may include productivity monitoring for medical procedures. A medical professional may use or have access to a computing device 125 during a medical procedure, before a medical procedure or after a procedure. The computing device 125 may be able to autonomously monitor the medical procedure or may receive inputs from the medical professional from time to time, such in preparation for beginning the procedure, during the procedure, or after the procedure. In a more specific example, the computing device may measure the time taken by the medical professional read an x-ray, CT scan, or other radiology scan. This timing can be tracked very closely because the files are opened, viewed, notations are made and then the case may be completed within a same application (e.g., PACS (picture archiving and communication system).

Medical procedure data may be received at the computing device 125 from a medical procedure data store 115 for a management device 110. The medical procedure data may include a metric, such as relative value units (RVUs) for example, associated with the medical procedure. In some examples, a metric or type of unit other than RVUs may be used to quantify and measure work performed by the medical professional.

Productivity data may be provided and updated in real time, and the productivity data may thus enable the medical professional to gauge performance for the day at any given time during the day to determine, for example, whether to try to work harder to meet a minimum daily goal or threshold number of RVUs (which goal/threshold may also be displayed with the productivity data). Productivity data may be monitored in real time using any of a variety of suitable methods. For example, the medical professional or an assistant to the medical professional, may enter progress associated with a degree of performance of the medical procedure, before, after or even at intervals during the medical procedure.

As another example, the local device may be part of a PACS (picture archiving and communication system) whereby the medical professional may review x-ray images, ultrasound images, or any of a variety of other types of moving (i.e. video) or still images. Analysis of the images and creation of evaluation notes may comprise the medical procedure. The medical professional may thus begin the procedure and the system may start a timer to time the medical professional's expenditure of time from the beginning of the evaluation until completion, such as when one case analysis is stopped, the evaluation notes are stored, the software program is exited, and so forth. The procedure may be begun with or without entering the code associated with the procedure. For example, the code may be automatically determined based on a software program accessed, a type of image accessed, initiation of a specified procedure and so forth.

Where the medical professional is using a display device for performance of the medical procedure, the productivity data may be displayed on the display device in an unobtrusive manner (e.g., small display, as an overlay, in a corner, including some transparency, etc.) or may be displayed on a second display device preferably in proximity to the display device used for the medical procedure to enable the medical professional to optionally view the productivity during performance of the medical procedure. For example, the local device 125 may include a display device 135 for displaying productivity monitored using the present technology (i.e., productivity monitor 130).

Presentation of the productivity data to the medical professional, even if presented at limited intervals during the day, may be useful to the medical professional to gauge how much money has been made, whether goals are being met, whether additional resources may continue to be expended for a medical procedure and so forth. Rather than relying on interpretation of medical codes by the management device 110, the medical codes being submitted via a network 120 during the day or at the end of the day, and receiving a report of productivity, such as at predetermined time intervals of weeks, months and so forth, the medical professional may substantially immediately ascertain the level of performance being completed in terms of productivity.

When the medical procedure has been completed, a procedure completion notification may be transmitted from the local device 125 to the management device 110 over the network 120. This notification may include the medical code entered by the medical professional for the medical procedure. The management device may use the medical code to calculate salary payments, productivity or any other desirable metric based on the submitted codes. The productivity data calculated and presented at the local device 125 may be independent of any calculation or interpretation of the data at the management device 110 and may be an unofficial representation of calculations or interpretations that may be performed at the management device. Presentation of the productivity data may be similar to reports created at the management device for the healthcare providing entity such as health maintenance organizations (HMOs), preferred provider organizations (PPOs) and so forth. The productivity data presented to the medical professional may be presented differently than for the healthcare providing entity. Optionally, the productivity data presentation may be configured or adapted to personal preferences of a particular medical professional. For example, a medical professional may desire to view a daily total RVU meter while hiding an hourly average RVU meter from being displayed.

A brief explanation of RVUs will now be provided as context for the present technology. Compensation provided medical professionals may be determined by the amount of RVUs the medical professional produces in a defined time frame, such as a calendar year. The number of RVUs a medical professional is able to complete may be at least partially dependent on geographic location, specialty of practice and other factors. In monetary terms, a medical professional may expect to earn on average approximately $35 to $45 per RVU when practicing in a primary care field, for example.

Each procedure completed by a medical professional may be assigned an RVU, which may be in whole RVUs or partial RVUs. For example, a 15 minute office visit may be assigned an RVU value of 0.6. If the medical professional receives $45 per RVU as compensation, the medical professional may earn $27 toward the medical professional's compensation for the year. RVUs may be based on factors other than time spent in performing a procedure. For example, while the 15 minute office visit may be 0.6 RVU, a 30 minute colonoscopy may be rated as 5 or 6 RVUs—thus being many times more valuable to the medical professional than the 0.6 RVU office visit.

The medical professional may have predetermined medical codes applied to the medical procedures to identify which medical procedures have been performed. A health care payer (e.g., a government organization or a HMO) may compensate the medical professional based on submission of a claim with a corresponding medical code for completion of the medical procedure. Various addition calculations, factoring, and so forth may be performed on the completed RVU submission, such as to convert the RVU to a dollar amount, to adjust the RVU and/or dollar amount by a geographical factor and so forth.

An RVU may include consideration of various different components of care and medical procedures performed. For example, an RVU for medical professional labor may consider time, skill, training and intensity for performing a specified medical procedure. This portion of the RVU, as with other portions, may be updated periodically to adjust for changes in the time, skill, training, intensity and so forth for the medical procedure. For example, many tasks that were previously more time consuming or intense in the past have now become easier, faster or even automated over time with advancements in medical technologies. As such, a number of RVUs for a medical procedure or a value of the RVUs may be increased or decreased based on changes in performance of the medical procedure. RVU codes with high RVU work may involve significant time, skill, intensity or combinations of time, skill and intensity. RVU values may be set differently for different specialties.

Practice expense RVUs may be another component of an overall RVU or RVU value. The practice expense component of the RVU may consider costs of maintaining a practice, including costs such as rent, equipment, supplies, staff costs (of individuals other than the medical professionals) and so forth. The practice expense RVU component may be calculated to include direct costs such as staff time, supplies and equipment time involved in performing the medical procedure, as well as indirect costs not directly attributable to the medical procedure, such as provision of a waiting room or billing service. The RVU code entered by the medical professional may have the practice expense RVU component assigned thereto based on a setting at which the procedure is performed, such as a hospital, clinic or the like. For example, practice expense compensation may be higher at non-hospital settings due to a higher expense of owning and operating equipment and providing staff resources.

RVUs may include a malpractice component. The malpractice component may represent payment for professional liability expenses. As with the professional work RVU component, the malpractice RVU component may be updated periodically based on malpractice issues, changes in insurance rates, changes in legislation and so forth. The malpractice RVU component may also consider the cost of medical practice on a geographical basis to account for differences in the cost of medical practice at different geographic locations in the country.

Entry of a medical code for a medical procedure may result in access of associated RVU data for the medical procedure. For example, the medical professional may enter a code for the medical procedure at a local workstation. The workstation may store a record of RVUs for the various potential codes the medical professional may enter or may retrieve the RVUs from a management device, such as a remote server for example. When the RVU data is stored locally the local device may periodically check for updates to the RVU data at the management device (e.g., at predetermined time intervals). Alternately, such updates may be pushed to the local device from the management device.

Medical professional productivity data related to the medical procedure may be provided for display at the computing device 125 based on the monitoring of the performance of the medical procedure and the medical procedure data including the RVU designation for the medical procedure. For example, the local device may have a display configured for displaying productivity data of the medical professional to the medical professional. In one example, virtual dials, gauges, or other interface gauge objects may be displayed to illustrate to the medical professional various aspects of productivity, such as a total number of RVUs completed for the day, an hourly RVU completion average, a procedure intensity designation, a monetary amount to be paid to the medical professional based on the completed RVUs, a projected monetary amount to be earned over a predetermined time period (such as the remainder of the day) based on past performance (such as earlier in the day or on previous days), a cost of performing the medical procedure, an amount payable for the procedure by a medical payer or an insurance provider for the patient and so forth. Productivity data may thus include various types of data which may be presented in any suitable manner. For example, rather than using dials or gauges, the productivity data may be presented as a bar chart, a table, a color, plain text or any other suitable form of presentation. The productivity data may be presented in a manner that is easily and quickly understandable by the medical professional.

Referring to FIGS. 2a-d, some example gauges are displayed for presenting various aspects of productivity information to the medical professional. The illustrated gauges are for example purposes and are not intended to be limiting. Gauges or other presentation styles may be configured for any type of data or according to any suitable preference.

Figure 2A:
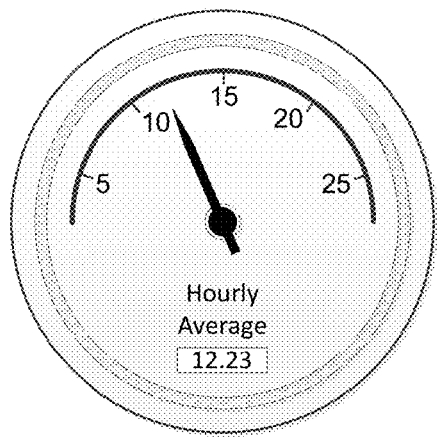
FIGS. 2a-2d are illustrations of productivity meters in accordance with examples of the present technology.

FIG. 2a illustrates an example hourly average RVU meter for displaying an average number of RVUs completed by the medical professional per hour over a predetermined period of time. For example, the predetermined period of time may be the current work day, a 24 hour period, a weekly average, a monthly average and so forth.

Figure 2B:
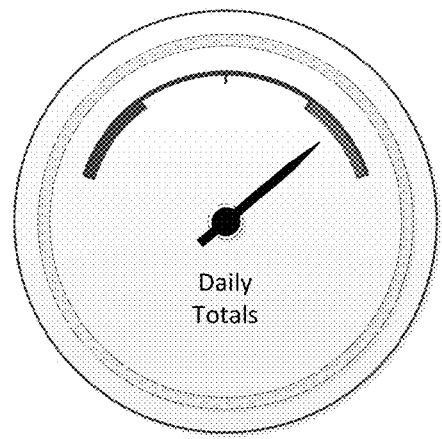

FIG. 2b illustrates a daily total RVU meter. The daily total may be a total number of RVUs completed on a calendar day, during a work period (which may span multiple days depending on the start time of the shift) and so forth. In one aspect, the daily totals meter may represent an average daily total over a defined period of time, such as a week or a month. The daily totals meter may include benchmarks for daily performance. For example, a portion at the left of the meter may represent an underperformance (e.g., red) or that a target number of RVUs for the day has not yet been reached. A portion at the right of the meter may represent a high performance of RVUs for the day (e.g., green). A middle meter portion in between the left and right meter portions may represent an acceptable range of neither underperformance nor overperformance.

Figure 2C:
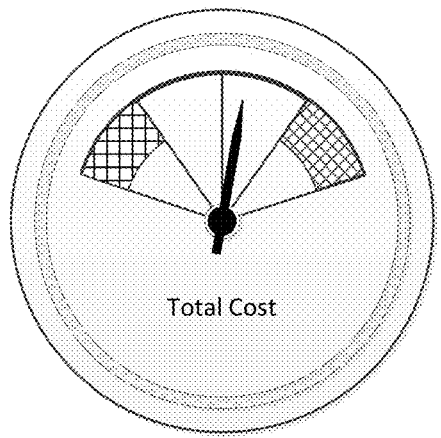

FIG. 2c illustrates a total cost RVU meter. A total cost may be calculated based on a number of different factors, such as have been described previously. For example, total costs may be calculate based on costs of the medical professional's time and services, costs for staff and materials, costs for the medical facility and so forth may be accumulated into a total cost per medical procedure to enable visualization of resource usage during the medical procedure. In some examples, the medical facility may be a private facility able and willing to provide medical services as long as insurance as available to defray at least a portion of the costs. Once a threshold has been reached, such as when the cost of the procedure meets or exceeds what is payable by an insurance company (plus any patient deductibles, out of pocket allowances or other factors), the facility may be alerted to address the payment issues with a patient directly. The total cost RVU meter may optionally be associated with blinking lights, alert audio sounds or the like to assist in notifying the medical professional that the threshold has been met or may be met soon. Usage of resources in performing a medical procedure may be tracked and entered into the local computing device as the resources are used to maintain the running total cost. A total running cost may be provided representing a total running cost for an individual procedure, for a patient undergoing a series of procedures and so forth. A total running cost may also represent a total amount payable by a medical payer relative to an amount of costs incurred.

Figure 2D:
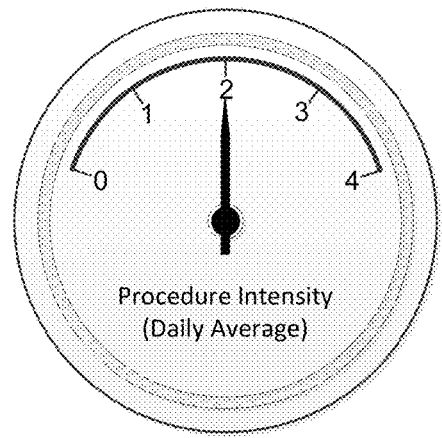

FIG. 2d illustrates a procedure intensity meter. The RVU data obtained from the management device may indicate a defined procedural intensity for each of the available medical procedures. The procedure intensity meter may be configured to visually display an indication to the medical professional as to the intensity of the current procedure. The intensity may be displayed on a scale, such as a scale from 0 to 4 in this example, with 4 representing a higher procedural intensity.

Figure 3:
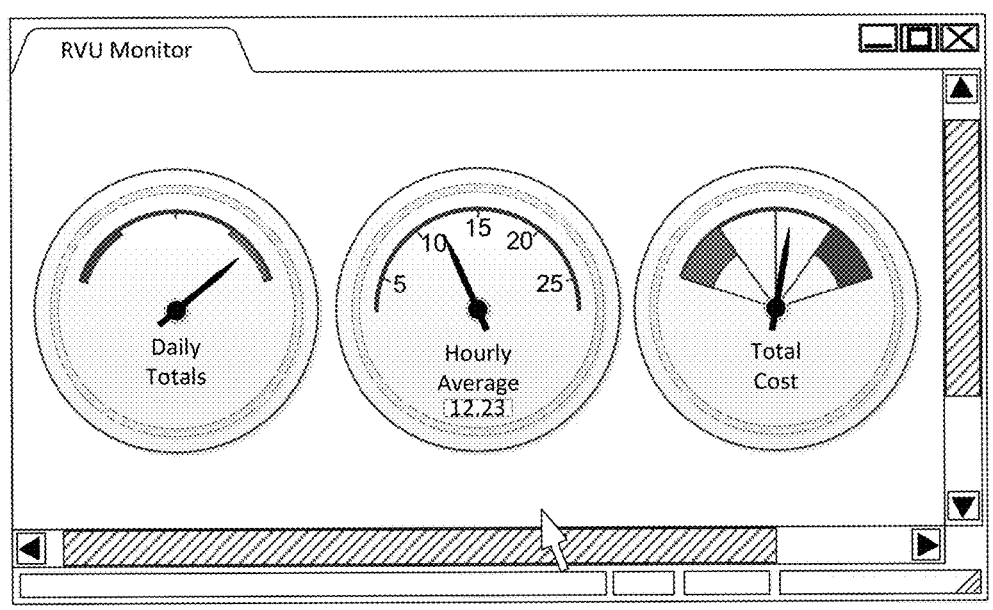
FIG. 3 is an illustration of a program interface simultaneously displaying multiple productivity meters in accordance with an example of the present technology.

FIG. 3 is an example page which may be displayed to the medical professional. The monitoring technology may be integrated into a PACS or other system already being used by the medical professional and typically available during performance of the medical procedures. Any number or any variety of productivity meters may be provided for display, and may be user configurable to suit individual preferences.

Figure 4:
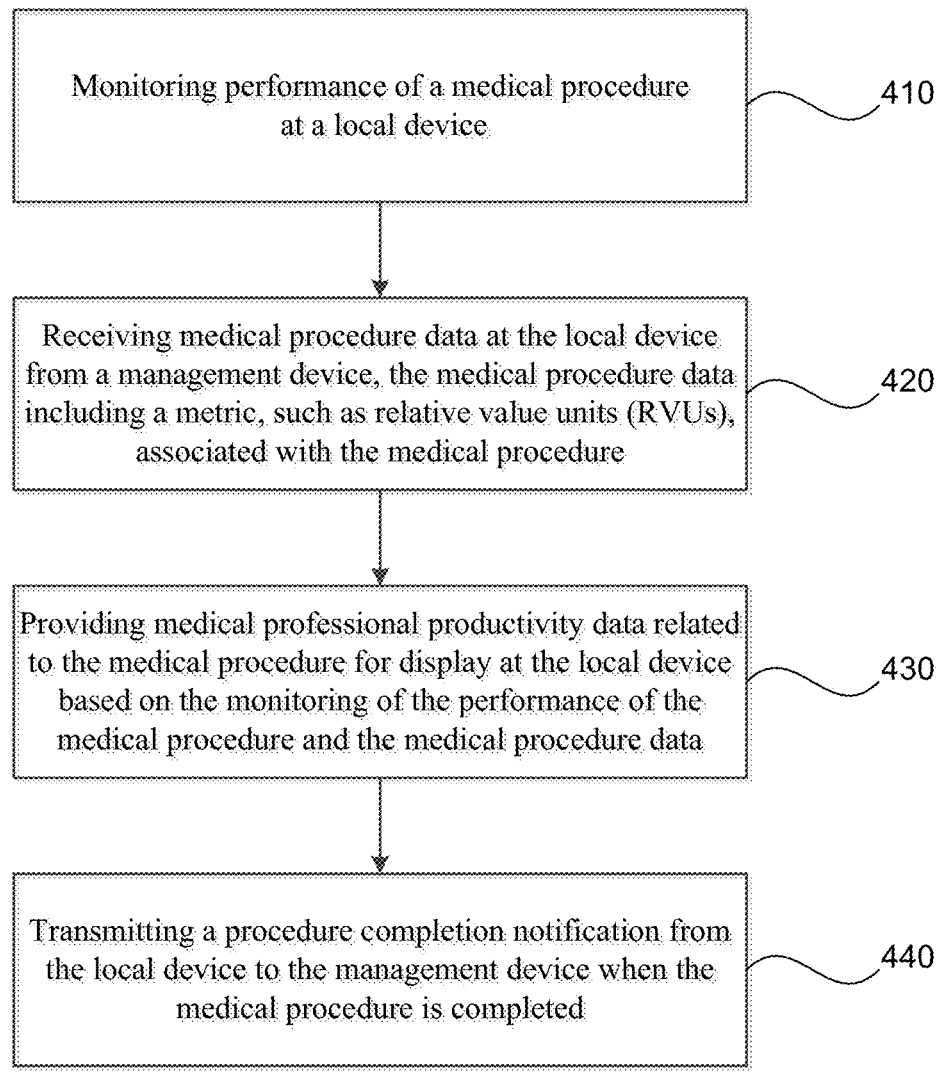
FIG. 4 is a flow diagram of a method for monitoring productivity in accordance with an example of the present technology.

Referring to FIG. 4, a flow diagram of a method for monitoring productivity is illustrated in accordance with an example of the present technology. The method may include monitoring 410 performance of a medical procedure at a local device. Medical procedure data may be received 420 at the local device from a management device. The medical procedure data may be received at the local device in response to a request from the local device or may be pushed to the local device from the management device. The medical procedure data received may include RVUs associated with the medical procedure and may be specific to a current procedure or may include any medical procedure data for any of the potential medical procedures that may be performed by the medical professional. The local device may identify the relevant medical procedure data from the data received from the management device for use in calculating productivity for the current medical procedure.

Further, the local device may be configured to locally or remotely store a productivity history for the medical professional in a data store for use in calculating averages, historical values, comparisons, running totals and so forth.

The method may further include providing 430 medical professional productivity data related to the medical procedure for display at the local device based on the monitoring of the performance of the medical procedure and the medical procedure data. The medical professional productivity data may be provided for display as the medical procedure progresses and may be provided for display concurrently with the performance of the medical procedure.

A procedure completion notification may be identified and transmitted 440 from the local device to the management device when the medical procedure is completed. In one aspect, the procedure status or progress may be transmitted to the management device during performance of the medical procedure. However, completion data may be more valuable at the management device as compared to immediate status updates. In contrast, the immediate productivity data may be more valuable to the medical professional than a monthly or quarterly report of productivity.

The method may include identifying a threshold medical professional productivity level representing a minimum target productivity level for a medical professional. The minimum threshold medical professional productivity level may be provided for display with the medical professional productivity data for comparison. The medical professional may be enabled to modify the threshold productivity displayed, which may optionally be independent of a threshold set or viewable by the medical facility, HMO or the like. For example, the medical facility may have a target daily total of 60 RVUs for the medical professional, but the medical professional may desire to set a personal goal of 80 daily RVUs. The productivity meter may optionally display both the fixed medical facility target and the personal goal. Also, the productivity meter may optionally display an aggregate productivity for a group of people, such as an average daily RVU for medical professionals working at a facility or for a specialization of medical professionals at the facility.

In one aspect, the method may include monitoring usage of resources with fixed costs. In conjunction with this monitoring, the method may include providing a total billable fee for the procedure less the fixed costs. In another aspect, the method may include providing a total billable fee for the procedure including the fixed costs. Identifying a total billable fee less the fixed costs may enable the medical professional to adjust the fee for the patient according to individual financial circumstances of the patient to ensure a higher likelihood of payment of the fee.

The present technology enables a immediate and accurate measurement of a specified medical procedure and may eliminate or reduce a potential falsification of time entered for the procedure when the PACS or other system is used to monitor actual time expended.

The present technology may enable medical professionals to better understand the RVU calculation for the geographical area and particular facility at which the medical profession is employed in meaningful terms which may assist in directing or focusing efforts of the medical professional and improving efficiency. The technology may enable the medical professional to determine whether efficiency/productivity targets are being met and may optionally compare the productivity of the medical professional with other colleagues or peers in the same facility or region through networked communication between devices or via the management device.

The technology may enable immediate viewing of profit margins of a running total cost of the medical procedure in view of an amount payable for the procedure by the insurance company. The technology may enable projection of cash flow, productivity or other metrics based on identification of past performance of the medical professional performing the current medical procedure.

Figure 5:
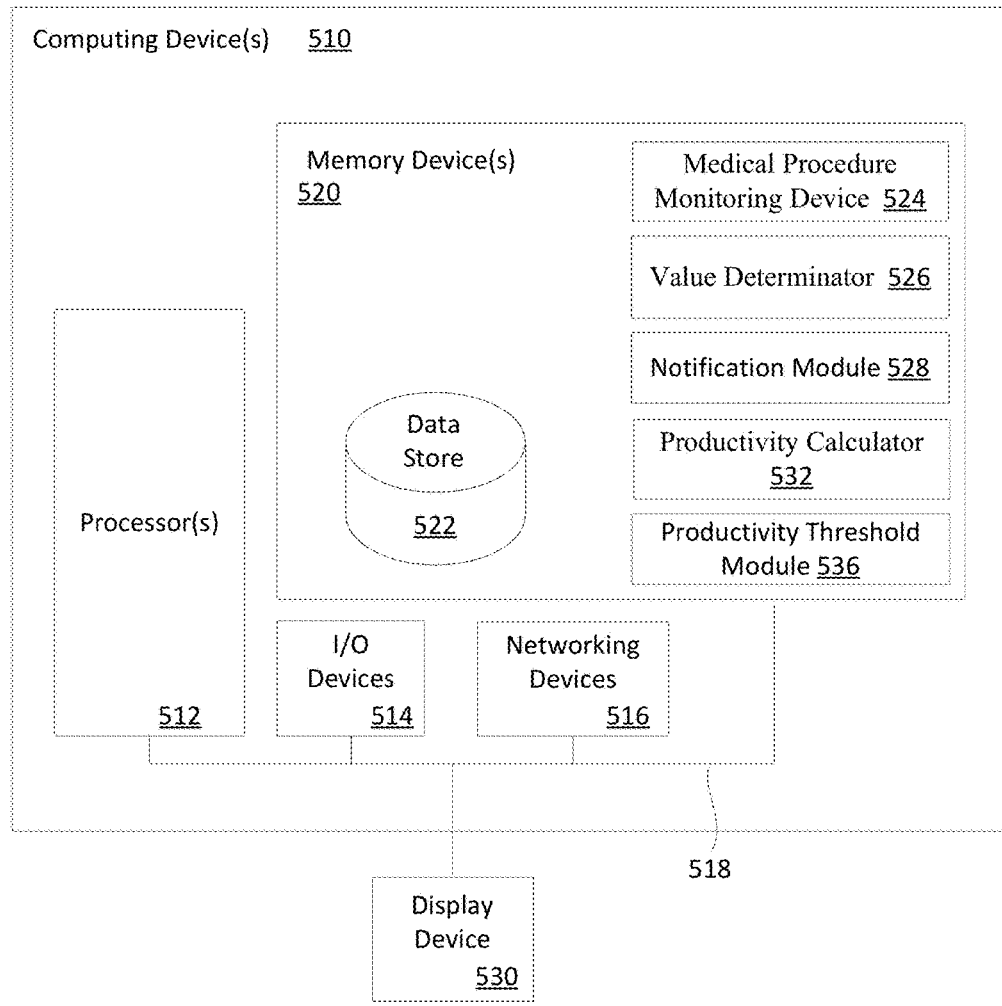
FIG. 5 is a block diagram of a productivity monitoring system in accordance with an example of the present technology.

Referring to FIG. 5, a block diagram of a productivity monitoring system is illustrated in accordance with an example. The system may include a medical procedure monitoring device 524 configured to identify a status of a medical procedure. For example, the status may be not started, in progress or completed. In one aspect, the status may be more specific, such as including a progress or percentage of completion of the medical procedure, usage of resources and so forth. The system may include a value determinator 526 configured to determine a relative value unit (RVU) associated with the medical procedure by retrieving the RVU from a management device. A productivity calculator 532 may be configured to calculate medical professional productivity data related to the medical procedure based on the status of the performance of the medical procedure and the determination of the RVU associated with the medical procedure. The system may include a notification module 528 configured to notify the management device when the status of the medical procedure is completed.

The system may include a display device 530 configured to display the medical professional productivity data concurrently with performance of the medical procedure. The display device 530 may also be configured to display the medical professional productivity data as a medical procedure intensity, a running daily total of RVUs, an average number of RVUs per unit of time, a monetary sum and so forth.

The system may include a productivity threshold module 536 configured to establish a minimum target productivity level for a medical professional and to provide the threshold medical professional productivity level for display with the medical professional productivity data for comparison. The productivity threshold module may enable the medical professional to modify the minimum target productivity level or create additional target productivity levels for meeting different goals.

The modules that have been described may be stored on, accessed by, accessed through, or executed by a computing device 510. The computing device 510 may comprise any system providing computing capability. The computing device 510 may be embodied, for example in the form of a client computer, a desktop computer, a laptop computer, a mobile device, a hand held messaging device, a set-top box, heads up display (HUD) glasses, a car navigation system, personal digital assistants, cellular telephones, smart phones, set-top boxes, network-enabled televisions, music players, web pads, tablet computer systems, game consoles, electronic book readers or other devices with like capability, including capabilities of receiving and presenting content from a server. The computing device 510 may include a display 530. The display 530 may comprise, for example, one or more devices such as cathode ray tubes (CRTs), liquid crystal display (LCD) screens, gas plasma based flat panel displays, LCD projectors, or other types of display devices, etc.

In one aspect, a plurality of computing devices may be employed that are arranged, for example, in one or more server banks, blade servers or other arrangements. For example, a plurality of computing devices together may comprise a cloud computing resource, a grid computing resource, and/or any other distributed computing arrangement. Such computing devices may be located in a single installation or may be distributed among many different geographical locations. For purposes of convenience, the computing device 510 is referred to herein in the singular form. Even though the computing device 510 is referred to in the singular form, however, it is understood that a plurality of computing devices may be employed in the various arrangements described above.

Various applications and/or other functionality may be executed in the computing device 510 according to various embodiments, which applications and/or functionality may be represented at least in part by the modules that have been described. Also, various data may be stored in a data store 522 that is accessible to the computing device. The data store 522 may be representative of a plurality of data stores as may be appreciated. The data stored in the data store 522, for example, is associated with the operation of the various applications and/or functional entities described. The components executed on the computing device 510 may include the modules described, as well as various other applications, services, processes, systems, engines or functionality not discussed in detail herein.

The term "data store" may refer to any device or combination of devices capable of storing, accessing, organizing and/or retrieving data, which may include any combination and number of data servers, relational databases, object oriented databases, simple web storage systems, cloud storage systems, data storage devices, data warehouses, flat files and data storage configuration in any centralized, distributed or clustered environment. The storage system components of the data store may include storage systems such as a SAN (Storage Area Network), cloud storage network, volatile or non-volatile RAM, optical media or hard-drive type media.

The computing device 510 may be representative of a plurality of local client devices that may be coupled to a network. The client devices may communicate over any appropriate network, including an intranet, the Internet, a cellular network, a local area network (LAN), a wide area network (WAN), a wireless data network or a similar network or combination of networks.

Although a specific structure may be described herein that defines server-side roles (e.g., roles of the management device) and client-side roles (e.g., roles of the local computing device), it is understood that various functions may be performed at the server side or the client side.

Certain processing modules may be discussed in connection with this technology. In one example configuration, a module may be considered a service with one or more processes executing on a server or other computer hardware. Such services may be centrally hosted functionality or a service application that may receive requests and provide output to other services or customer devices. For example, modules providing services may be considered on-demand computing that is hosted in a server, cloud, grid or cluster computing system. An application program interface (API) may be provided for each module to enable a second module to send requests to and receive output from the first module. Such APIs may also allow third parties to interface with the module and make requests and receive output from the modules. Third parties may either access the modules using authentication credentials that provide on-going access to the module or the third party access may be based on a per transaction access where the third party pays for specific transactions that are provided and consumed.

The computing device 510 may include one or more processors 512 that are in communication with memory devices 520. The computing device 510 may include a local communication interface for the components in the computing device 510. For example, the local communication interface may be a local data bus 518 and/or any related address or control busses as may be desired.

The memory device 520 may contain modules that are executable by the processor(s) and data for the modules. Located in the memory device 520 are modules executable by the processor 512. The data store 522 may also be located in the memory device 520 for storing data related to the modules and other applications along with an operating system that is executable by the processor(s) 512.

Various applications may be stored in the memory device and may be executable by the processor(s) 512. Components or modules discussed in this description that may be implemented in the form of software using high programming level languages that are compiled, interpreted or executed using a hybrid of the methods.

The computing device 510 may also have access to I/O (input/output) devices 514 that are usable by the computing devices 510. An example of an I/O device 514 is a display screen that is available to display output from the computing devices. Other known I/O devices 514 may be used with the computing device 510 as desired. Networking devices 516 and similar communication devices may be included in the computing device 510. The networking devices 516 may be wired or wireless networking devices that connect to the internet, a LAN, WAN, or other computing network.

The components or modules that are shown as being stored in the memory device 520 may be executed by the processor 512. The term "executable" may mean a program file that is in a form that may be executed by a processor. For example, a program in a higher level language may be compiled into machine code in a format that may be loaded into a random access portion of the memory device and executed by the processor, or source code may be loaded by another executable program and interpreted to generate instructions in a random access portion of the memory to be executed by a processor. The executable program may be stored in any portion or component of the memory device. For example, the memory device may be random access memory (RAM), read only memory (ROM), flash memory, a solid state drive, memory card, a hard drive, optical disk, floppy disk, magnetic tape, or any other memory components.

The processor 512 may represent multiple processors and the memory may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology. As used herein, the terms "medium" and "media" may be interchangeable with no intended distinction of singular or plural application unless otherwise explicitly stated. Thus, the terms "medium" and "media" may each connote singular and plural application.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The invention claimed is:

1. A method for displaying monitored productivity in real time, comprising:
    monitoring performance of a medical procedure at a local device by: detecting usage of a medical device or software application, detecting file access, or receiving input from a medical professional; and determining an expenditure of time associated with the performance of the medical procedure;
    receiving medical procedure data at the local device from a management device, the medical procedure data including a number of relative value units (RVUs) associated with the medical procedure;
    identifying a procedure completion notification from the local device when the performance of the medical procedure is completed; and
    displaying medical professional productivity data related to the medical procedure at the local device based on the monitoring of the performance of the medical procedure and the medical procedure data, wherein the medical professional productivity data is based on time expended performing the medical procedure and the number of RVUs assigned to the medical procedure and is represented as RVUs/time;
    wherein displaying the medical professional productivity data comprises:
        displaying a plurality of dials or gauges arranged in a series in a graphical user interface;
        displaying in one of the plurality of dials or gauges a unit of the RVUs for a defined period of time;
        displaying in another one of the plurality of dials or gauges a cost of the medical procedure as determined at least from the expenditure of time and the number of RVUs associated with the medical procedure; and
        updating the plurality of dials or gauges in real time based on changes to the performance of the medical procedure, identification of additional medical procedure data, or receipt of the procedure completion notification.

2. The method of claim 1, wherein the medical professional productivity data provided for display at the local device comprises a display of the medical professional productivity data concurrently with the performance of the medical procedure, the method further comprising providing visual or audio notifications at the local device when the medical professional productivity data nears a threshold medical professional productivity level.

3. The method of claim 1, further comprising updating the medical professional productivity data in real time as the medical procedure progresses and providing visual or audio notifications at the local device when a threshold medical professional productivity level has been met.

4. The method of claim 1, wherein the medical procedure data further comprises an intensity designation associated with the medical procedure, the method further comprising providing a separate visual display of the intensity designation at the local device with the medical professional productivity data.

5. The method of claim 4, wherein the intensity designation includes a procedure intensity of the medical procedure as determined from the medical procedure data received from the management device and an average intensity of medical procedures performed within a defined period of time.

6. The method of claim 1, wherein the medical professional productivity data comprises a running daily total of RVUs.

7. The method of claim 1, wherein the medical professional productivity data comprises an hourly average of RVUs.

8. The method of claim 1, wherein the medical professional productivity data comprises a monetary sum including costs for time, services and materials, and wherein receiving the medical procedure data at the local device from a management device is in response to transmitting a code for the medical procedure from the local device, wherein the number of RVUs and a portion of the monetary sum are associated with the code, and another portion of the monetary sum is generated based on resource usage as the medical procedure progresses; the method further comprising providing a notification when the monetary sum exceeds what is payable by an insurance company for the medical procedure.

9. The method of claim 1, further comprising:
    identifying a threshold medical professional productivity level representing a minimum target productivity level for a medical professional and providing the threshold medical professional productivity level for display with the medical professional productivity data for comparison; and
    identifying at least one additional target productivity level representing at least one goal of the medical professional and providing the additional target productivity level for display with the threshold medical professional productivity level and the medical professional productivity data.

10. The method of claim 9, further comprising enabling a medical professional to modify the threshold productivity and the at least one additional target productivity level.

11. The method of claim 1, wherein monitoring performance of the medical procedure at the local device further comprises monitoring usage of resources with fixed costs, the method further comprising:
providing a total billable fee for the procedure less the fixed costs for display.

12. The method of claim 1, wherein monitoring performance of the medical procedure at the local device further comprises monitoring usage of resources with fixed costs, the method further comprising:
providing a total billable fee for the procedure including the fixed costs for display.

13. A productivity monitoring system, comprising:
a medical procedure monitoring device to identify a status of a medical procedure by: detecting usage of a medical device or software application, detecting file access, or receiving input from a medical professional; and determining an expenditure of time associated with performance of the medical procedure; and
a non-transitory computer-readable medium comprising computer-executable instructions which, when executed by a processor:
determine a number of relative value units (RVUs) associated with the medical procedure by retrieving the number from a management device where numbers assigned to medical procedures are stored;
calculate medical professional productivity data related to the medical procedure based on the status of the performance of the medical procedure and the determination of the RVUs associated with the medical procedure, wherein the medical professional productivity data is based on the time expended performing the medical procedure and the number of RVUs assigned to the medical procedure and is represented as RVUs/time;
notify the management device when the status of the medical procedure is completed; and
display medical professional productivity data related to the medical procedure based on the monitoring of the performance of the medical procedure and the medical procedure data, wherein the medical professional productivity data is based on time expended performing the medical procedure and the number of RVUs assigned to the medical procedure and is represented as RVUs/time;
wherein the medical professional productivity data is displayed by:
displaying a plurality of dials or gauges arranged in a series in a graphical user interface;
displaying in one of the plurality of dials or gauges a unit of the RVUs for a defined period of time;
displaying in another one of the plurality of dials or gauges a cost of the medical procedure as determined at least from the expenditure of time and the number of RVUs associated with the medical procedure; and
updating the plurality of dials or gauges in real time based on changes to the performance of the medical procedure, identification of additional medical procedure data, or receipt of a procedure completion notification.

14. The system of claim 13, further comprising a display device, wherein the display device displays the medical professional productivity data concurrently with performance of the medical procedure.

15. The system of claim 13, wherein the display device displays the medical professional productivity data as a medical procedure intensity, a running daily total of RVUs, an average number of RVUs per unit of time, or a monetary sum.

16. The system of claim 13, wherein the instructions, when executed by the processor, further establish a minimum target productivity level for a medical professional and to provide a threshold medical professional productivity level for display with the medical professional productivity data for comparison.

17. A computer program product embedded in a computer-readable medium for monitoring productivity, the computer program product including instructions that, when executed by a processor, cause the processor to
monitor performance of a medical procedure at a local device by: detecting usage of a medical device or software application, detecting file access, or receiving input from a medical professional; and determining an expenditure of time associated with the performance of the medical procedure;
retrieve medical procedure data from a management device, the medical procedure data including a number of relative value units (RVUs) associated with the medical procedure;
provide medical professional productivity data related to the medical procedure for display at the local device based on the monitoring of the performance of the medical procedure and the medical procedure data, wherein the medical professional productivity data is based on time expended performing the medical procedure and the number of RVUs assigned to the medical procedure and is represented as RVUs/time;
transmit a procedure completion notification from the local device to the management device when the performance of the medical procedure is completed; and
display medical professional productivity data related to the medical procedure based on the monitoring of the performance of the medical procedure and the medical procedure data, wherein the medical professional productivity data is based on time expended performing the medical procedure and the number of RVUs assigned to the medical procedure and is represented as RVUs/time;
wherein the medical professional productivity data is displayed by:
displaying a plurality of dials or gauges arranged in a series in a graphical user interface;
displaying in one of the plurality of dials or gauges a unit of the RVUs for a defined period of time;
displaying in another one of the plurality of dials or gauges a cost of the medical procedure as determined at least from the expenditure of time and the number of RVUs associated with the medical procedure; and
updating the plurality of dials or gauges in real time based on changes to the performance of the medical procedure, identification of additional medical procedure data, or receipt of the procedure completion notification.

18. The computer program product according to claim 17, further including instructions that, when executed by the processor, cause the processor to provide the medical professional productivity data for display concurrently with the performance of the medical procedure.

19. The computer program product according to claim 17, further including instructions that, when executed by the processor, cause the processor to provide the medical professional productivity data for display to appear as a plurality of medical professional-configurable productivity dials.

20. The computer program product according to claim 17, further including instructions that, when executed by the processor, cause the processor to monitor an expenditure of time by a medical professional performing the medical procedure, identify a billing rate of the medical professional, and calculate a time cost based on the expenditure of time and the billing rate.

* * * * *